United States Patent [19]

Ecke, Jr.

[11] Plant 4,952

[45] Nov. 16, 1982

[54] POINSETTIA NAMED RED CURLY

[75] Inventor: Paul Ecke, Jr., Encinitas, Calif.

[73] Assignee: Paul Ecke Ranch, Encinitas, Calif.

[21] Appl. No.: 255,821

[22] Filed: Apr. 20, 1981

[51] Int. Cl.[3] ..... A01H 5/00

[52] U.S. Cl. ..... Plt./86

[58] Field of Search ..... Plt./86

*Primary Examiner*—Robert E. Bagwill

*Attorney, Agent, or Firm*—Chas. W. Rummler

[57] ABSTRACT

A new poinsettia cultivar of the curly type originating as a hybrid seedling and being distinguished by the dark red color of its bracts and the unique shape of the leaves and bracts which are abundant in number and are carried on strong, straight stems of medium height, the bracts being in a generally imbricated arrangement and forming a round cushion-like appearance with a diameter of from about 5 to 7½ inches.

2 Drawing Figures

BACKGROUND OF THE NEW PLANT

This new poinsettia was produced as a hydrid by crossing various seedlings or mutations, including Ecke's Flaming Sphere (U.S. Plant Pat. No. 1,052), at my breeding facilities at Encinitas, Calif., and this variety was selected by me from many red curly seedlings because it was the best red. I reproduced this plant in my greenhouse at Encinitas by cuttings and carried on such propagation through several successive generations which demonstrated that the novel characteristics of this plant would hold true from generation to generation and appear to be firmly fixed.

DESCRIPTION OF THE DRAWINGS

This new poinsettia plant is illustrated by the accompanying full color photographic drawings, of which the upper view shows a pair of potted plants of this variety in side elevation and the lower view shows the same plants as seen when looking downwardly from above the plants, the colors shown being as nearly true as is reasonably possible to obtain by professional photographic procedures.

DESCRIPTION OF THE NEW PLANT

The following is a description of this new poinsettia cultivar as observed in greenhouse at Encinitas, Calif., the color designations being according to The R.H.S. Colour Chart published by The Royal Horticultural Society of London, England.

THE PLANT

Origin: Seedling.

Parentage: Unknown, but Ecke's Flaming Sphere (U.S. Plant Pat. No. 1,052) is in the generation line.

Classification:

*Botanic.*—*Euphorbia pulcherrima.*

*Commercial.*—Pot poinsettia.

Form: Shrub.

Height: Medium.

Growth habit: Vigorous with little natural tendency to branch. After a stem is pinched back, only two or three branches will form. Cuttings from this plant produce roots under greenhouse conditions the same as with other poinsettias.

Growth rate: Normal for poinsettias.

Foliage: Abundant in quantity.

*Leaf shape.*—The shape is predominantly ovate and often dentated. Most leaves are mono or bi-lobed on each side of the midrib and the midrib is convoluted through about 30° to 120° of arc with the upper surface of the leaf being the outer surface of the curve.

*Leaf size.*—The leaves average about 3 to 5 inches long as measured along the midrib and about 3 to 5 inches wide.

*Aspect.*—Upper side — Dull with veins indented. Under side — Dull with ordinary veining.

*Color.*—Upper side — Between RHS 139A and 147A but somewhat darker. Under side — Between RHS 137A and 137B.

*Retention.*—Good, but not as long as the Hegg type of poinsettias.

Bracts: The bracts form a round cushion-like appearance with an average diameter of from 5 to 7½ inches. The bracts are in a generally imbricated arrangement and the individual bract tips form a counter-clockwise swirl when looking down onto the top of the plant.

*Shape.*—The shape of the bracts is generally ovate but with a long acuminate tip.

*Size.*—The bracts are usually in the range of 2½ to 4 inches long.

*Color.*—Upper side — Between RHS 45A and 46B. Under side — Near RHS 46C.

*Ribs and veins.*—The ribs and veins are near the color of the bracts and are therefore inconspicuous.

*Petioles.*—The petioles are quite short, about ¼ to ½ inches long, and are inconspicuous.

*Retention.*—Good. The bracts last longer than the leaves.

This cultivar is unique as a poinsettia because of the leaf and bract shape, which may be described as being puckered and curled as though caused by the foreshortening of the leaf midrib as by pulling a drawstring inside the midrib.

I claim:

1. A new and distinctive poinsettia cultivar, substantially as herein shown and described, distinguished by the unique puckered and curled shape of the leaves and bracts, the bracts having a solid and overall dark red color and being in a generally imbricated arrangement so as to form a cushion-like appearance around the flowers of the plant.

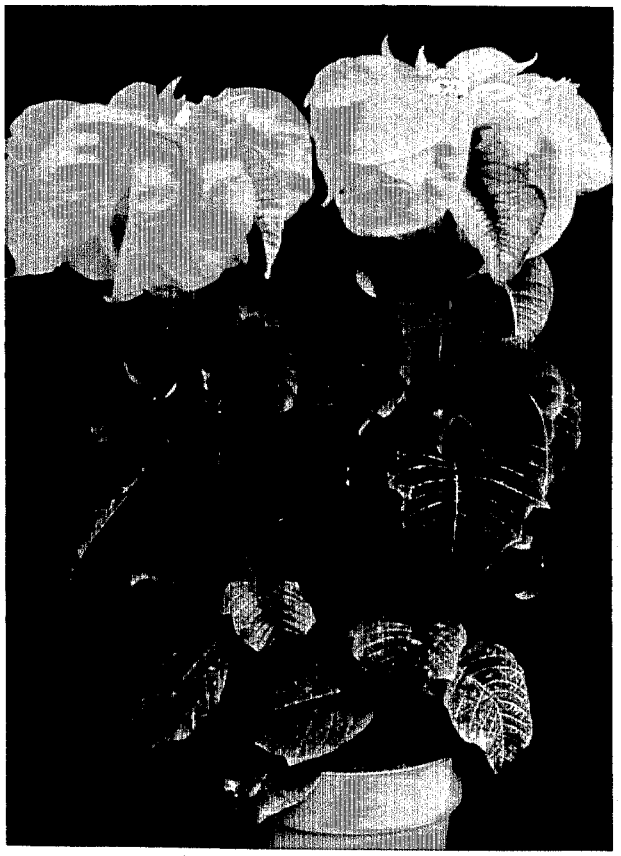
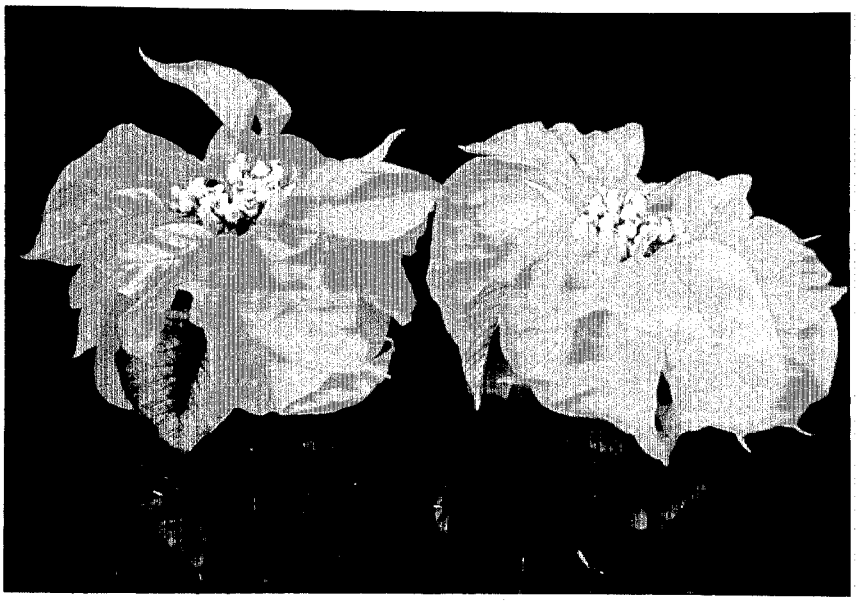

* * * * *